(12) United States Patent
Gershteyn

(10) Patent No.: US 6,962,153 B2
(45) Date of Patent: Nov. 8, 2005

(54) INTERLOCK/EXCLUSION SYSTEMS FOR MULTIPLE VAPORIZER ANESTHESIA MACHINES

(75) Inventor: Jacob Gershteyn, Newtown, PA (US)

(73) Assignee: Draeger Medical, Inc., Telford, PA (US)

( * ) Notice: Subject to any disclaimer, the term of this patent is extended or adjusted under 35 U.S.C. 154(b) by 204 days.

(21) Appl. No.: 10/681,787

(22) Filed: Oct. 7, 2003

(65) Prior Publication Data

US 2005/0072420 A1 Apr. 7, 2005

(51) Int. Cl.[7] .............................................. A61M 16/00
(52) U.S. Cl. ........................... 128/203.12; 128/203.13; 128/202.22; 261/DIG. 65
(58) Field of Search ..................... 128/202.22, 203.12, 128/203.13, 203.14, 203.24, 203.19; 137/637.1; 74/483 K; 261/DIG. 65

(56) References Cited

U.S. PATENT DOCUMENTS

| | | | | |
|---|---|---|---|---|
| 3,703,172 A | * | 11/1972 | Hay | 128/200.13 |
| 4,246,115 A | * | 1/1981 | Swank | 210/168 |
| 4,307,718 A | | 12/1981 | Schreiber | |
| 4,308,865 A | * | 1/1982 | Hay | 128/200.14 |
| 4,346,701 A | * | 8/1982 | Richards | 128/200.14 |
| 4,434,790 A | * | 3/1984 | Olesen | 128/200.14 |
| 4,463,754 A | | 8/1984 | McDonald | |
| 4,493,318 A | | 1/1985 | Mohr et al. | |
| 4,759,358 A | | 7/1988 | Gregory | |
| 4,932,398 A | | 6/1990 | Lancaster et al. | |
| 4,982,734 A | * | 1/1991 | Green et al. | 128/200.14 |
| 5,520,168 A | | 5/1996 | Whitaker | |
| 5,537,992 A | * | 7/1996 | Bjoernstijerna et al. | 128/203.14 |
| 5,657,747 A | | 8/1997 | Holliday | |
| 6,302,104 B1 | | 10/2001 | Kronekvist | |

FOREIGN PATENT DOCUMENTS

| | | |
|---|---|---|
| GB | 1 385 670 | 2/1975 |
| GB | 2 052 271 | 1/1981 |

* cited by examiner

Primary Examiner—Henry Bennett
Assistant Examiner—Dinnatia Doster-Greene
(74) Attorney, Agent, or Firm—Caesar, Rivise, Bernstein, Cohen & Pokotilow, Ltd.

(57) ABSTRACT

A gas administration apparatus, e.g., anesthesia machine, making use of three or more gas flow, e.g., vaporizer, units removably mounted thereon by an interlock exclusion system. The interlock/exclusion systems is operative to prevent opening of any gas flow unit if one gas flow unit is already open and irrespective of how many gas flow units are mounted on the apparatus at the time.

27 Claims, 2 Drawing Sheets

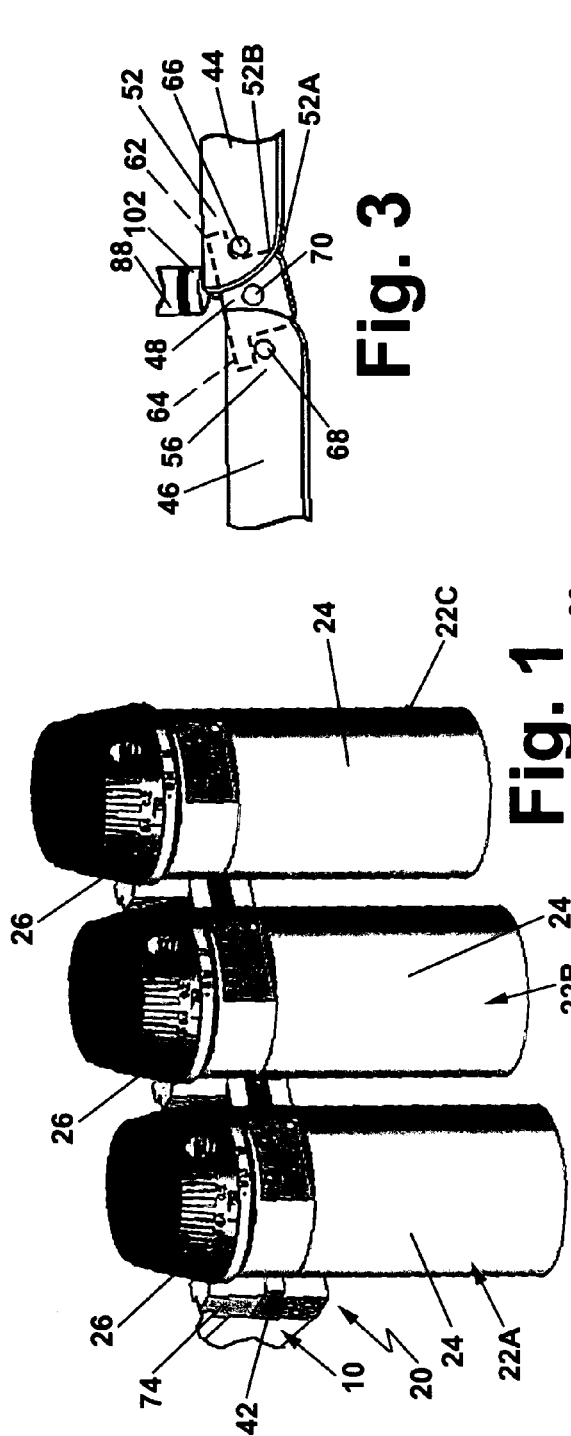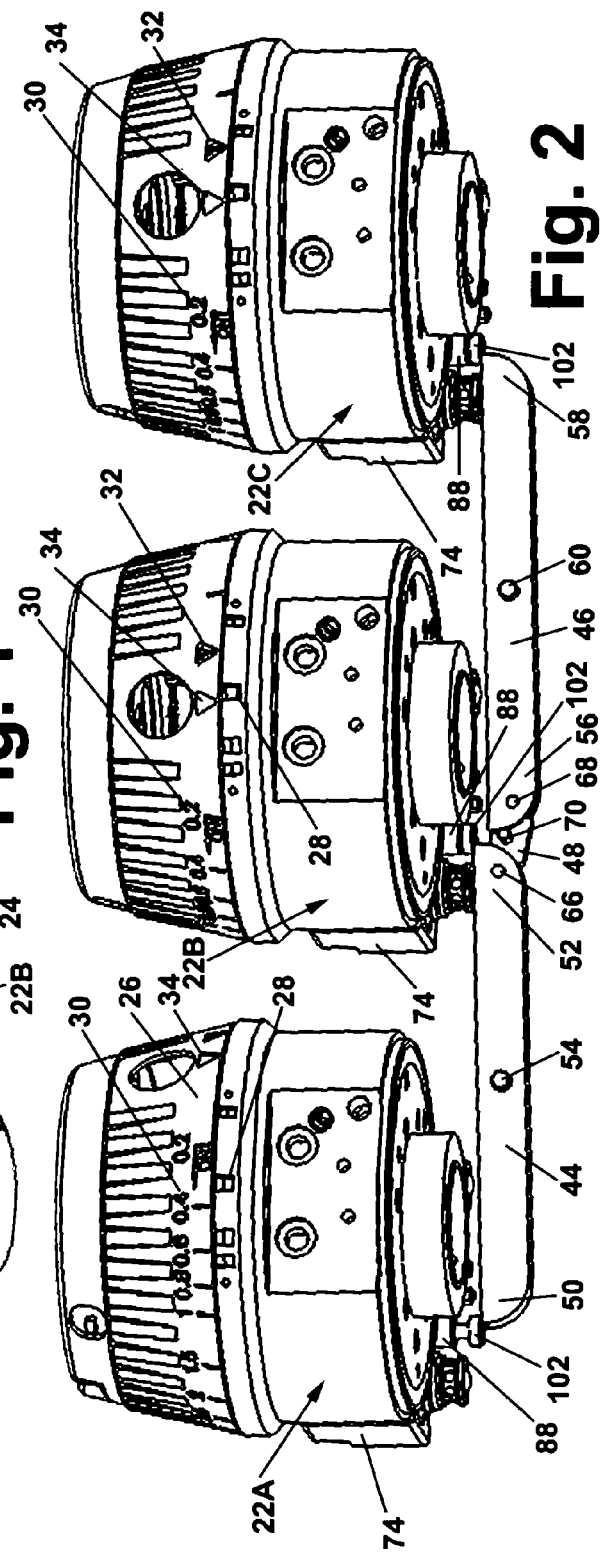

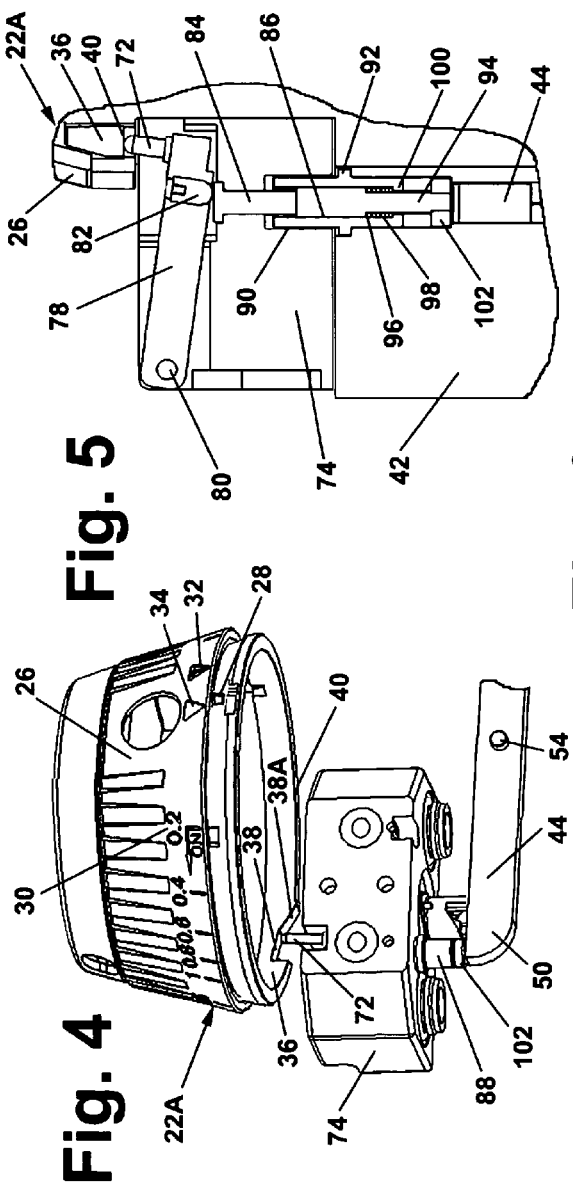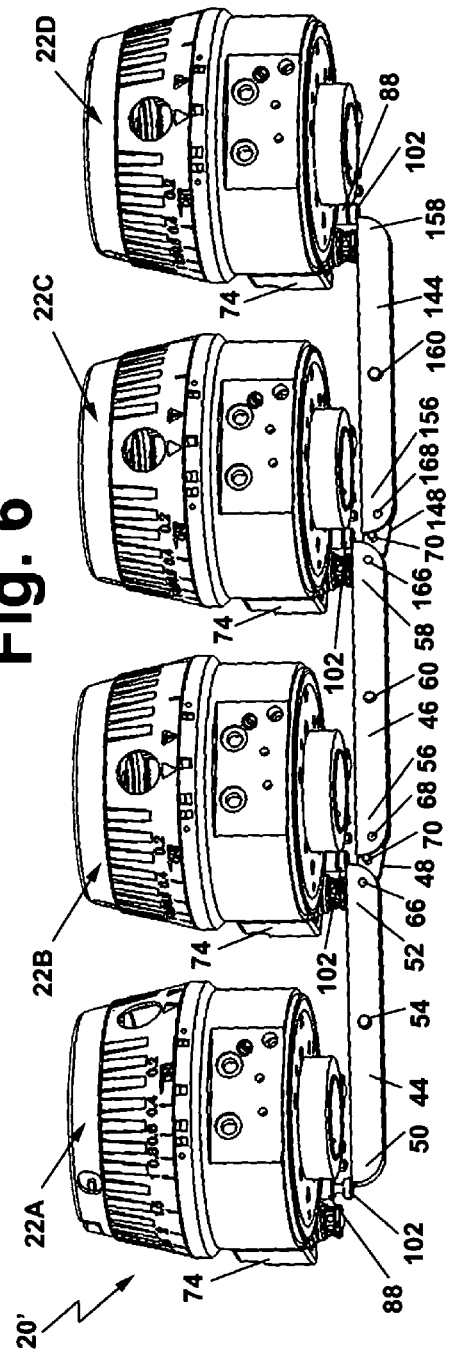

INTERLOCK/EXCLUSION SYSTEMS FOR MULTIPLE VAPORIZER ANESTHESIA MACHINES

BACKGROUND OF THE INVENTION

1. Field of Invention

This invention relates generally to gas administration apparatus, e.g., anesthesia machines, and more particularly to interlocks or exclusion systems for use with such apparatus having multiple gas flow units, e.g., vaporizers, to prevent more than one gas flow unit from being opened at the same time.

2. Description of Related Art

It is common practice for an anaesthesia apparatus to have mounted on it two or more separate vaporizers, each arranged for delivering different volatile anaesthetic so that the same basic anaesthesia apparatus can be used during a series of surgical operations to meet the needs of different patients.

In U.S. Pat. No. 4,307,718 (Schreiber), which is assigned to the same assignee as this invention and whose disclosure is incorporated by reference herein, there is disclosed an interlock device for a pair of vaporizers of an anesthesia machine. Each vaporizer includes a rotary dial for establishing the vapor concentration provided. The interlock device insures that one vaporizer is closed whenever the other is open and comprises a pair of reciprocable pins and a cooperating pivotable lever. Each pin is arranged to be extended into a cam recess in the vaporizer dial by the pivoting action of the lever. Rotation of one dial automatically causes the pin located therein to move out of the cam recess and into contact with the lever. This action pivots the lever and causes it to contact the other pin to extend the other pin into the recess in the associated vaporizer dial, thereby locking the dial closed.

The assignee of this invention has sold anesthesia machines, e.g., the Narkomed® 2A device, making use of three non-removable vaporizers and an exclusion or interlock system for preventing more than one such vaporizer to be opened at any one time. The exclusion system used in that machine basically comprises three pivotable bars, one long one and two short ones. The two short bars are located end to end in front of the long bar. Each bar is arranged to pivot in a horizontal plane about its midpoint. The two short pivot bars are located immediately behind the rotatable caps of three side-by-side, non-removable vaporizers. Each vaporizer cap includes a cam slot or recess in which one end of a respective reciprocating pin is located. The free end of the pin for the leftmost vaporizer is located adjacent the leftmost end of the left side short pivoting bar and is arranged to engage it when the leftmost vaporizer is used. In still a similar manner free end of the pin for the rightmost vaporizer is located adjacent the rightmost end of the right side short pivoting bar and is arranged to engage it when the rightmost vaporizer is used. The free end of the pin for the middle vaporizer is located adjacent the rightmost end of the left short pivoting bar and the leftmost end of the right side short pivoting bar to engage both of those ends when the middle vaporizer is used. The long bar includes a pair of pins or set screws attached to each end and projecting outward therefrom. The pin on the leftmost end of the long pivoting bar is arranged to be engaged by the leftmost end of the left short pivoting bar. In a similar manner the pin on the rightmost end of the long pivoting bar is arranged to be engaged by the rightmost end of the right short pivoting bar. Operation of that exclusion system for each of the three vaporizers is as follows: all of the vaporizers should be off, i.e., their caps turned to the off position, before any particular vaporizer is opened. For example, if the rightmost vaporizer is to be used, the rotation of its cap causes the pin associated with it to move rearward, thereby engaging the rightmost end of the right short pivoting bar. This action pivots that bar counter-clockwise to bring its rightmost end into engagement with the projecting setscrew on the rightmost end of the long pivoting bar, thereby causing that bar to pivot counter clockwise. The pivoting of the right short bar brings its left end into engagement with the pin for the middle vaporizer, thereby holding it in position whereupon the pin is located within the cam recess of the vaporizer cap, to thereby prevent it from being turned (opened). The pivoting of the long bar brings its setscrew on its left end into engagement the leftmost end of the left short pivoting bar, thereby pivoting the left short bar counterclockwise, whereupon it engages the pin for the leftmost vaporizer, thereby holding that pin in position within the cam recess of the leftmost vaporizer cap to prevent the cap from being turned (opened). If the leftmost vaporizer is to be used, all of the vaporizers must be turned to the off position. Then the leftmost vaporizer can be opened. The operation of opening the leftmost vaporizer is similar to the operation of opening the rightmost vaporizer, except that the two short bars and one long bar are pivoted in the opposite directions to prevent the pins from the middle and rightmost vaporizers from exiting their respective cam recesses. If the middle vaporizer is to be used, all of the vaporizers must be turned to the off position. Then the middle vaporizer can be opened. In particular, the cap of the middle vaporizer is rotated to an open position, whereupon its pin is moved backward to thereby engage the rightmost end of the left short pivoting bar and the leftmost end of the right short pivoting bar. This causes the left short bar to pivot counterclockwise and the right short bar to pivot clockwise. The pivoting of the left short bar counterclockwise causes its left end to engage the pin associated with the leftmost vaporizer to hold it in position within the cam recess of the leftmost vaporizer cap to prevent that cap from being turned. In a similar manner, the pivoting of the right short bar clockwise causes its right end to engage the pin associated with the rightmost vaporizer to hold it in position within the cam recess of the rightmost vaporizer cap to prevent that cap from being turned.

In United Kingdom patent specification No. 1,385,670, there is described a gas administration apparatus on which one or more gas flow units can be mounted in a removable plug-in fashion.

In United Kingdom patent No. 2,052,271, there is described an interlocking system which prevents two different anaesthetic being delivered to a patient at the same time or otherwise becoming mixed. This known interlocking system includes pins associated with each vaporizer which, when its concentration dial is moved from the off position, causes the pins to extend outwardly and block the movement of corresponding pins on immediately adjacent vaporizers thereby preventing the concentration dials of these other vaporizers from being operated. With this arrangement it is impossible to switch more than one vaporizer into a gas circuit at any one time. While this known interlocking system works well when there are two or more units arranged side-by-side, if the middle unit of, for example, three units is removed for any reason then the interlocking action of the first unit cannot be transmitted to the third unit and vice versa. One solution to this problem involves using non-functional (dummy) second units or merely applying warning labels to indicate that no interlocking system is available.

In U.S. Pat. No. 4,759,358 (Gregory) there is disclosed an interlock system for use with two or more gas flow units (vaporizers) when mounted in plug-in fashion on the back bar of an anaesthesia machine. Each unit includes a rotary cap, which when moved from an off to an operative position admits to the unit a gas from a supply provided by the apparatus. The interlock system includes at least one pin associated with each gas flow unit which, when the rotary cap is moved towards its operative position, extends outwardly from the unit to engage and move a spacer mounted for sliding movement on the apparatus between adjacent units towards a similar adjacent unit thereby to prevent the rotary cap of the similar adjacent unit being moved towards its operative position.

Other United States Patents disclosing anesthesia apparatus including interlocks/exclusion systems for preventing more than one vaporizer from being opened at any one time are: U.S. Pat. No. 4,463,754 (McDonald); U.S. Pat. No. 4,493,318 (Mohr et al.); U.S. Pat. No. 4,932,398 (Lancaster et al.); U.S. Pat. No. 5,520,168 (Whitaker); U.S. Pat. No. 5,657,747 (Holliday); and U.S. Pat. No. 6,302,104 (Kronekvist).

While the above interlocks/exclusion systems may be generally suitable for their intended purposes, they exhibit one or more of the following drawbacks, e.g., complexity, ease of use, limited number of vaporizers that can be accommodated, etc.

All references cited herein are incorporated herein by reference in their entireties.

BRIEF SUMMARY OF THE INVENTION

An interlock/exclusion system for use with a gas administration apparatus, e.g., an anesthesia machine, having at least a first, second and third gas flow, e.g., vaporizer, units removably secured thereto. Each of the gas flow units is arranged to be opened to enable the apparatus to provide a gas to a patient. The interlock/exclusion system is arranged when any one of the gas flow units is opened to prevent the opening of the others of the gas flow units.

The interlock/exclusion system basically comprises a first pivotable bar, a second pivotable bar, a first pivotable coupling, a first pin associated with the first bar and with the first gas flow unit, a second pin associated with the first and second bars and the second gas flow unit, a third pin associated with the second bar and the third gas flow unit. The first pivotable bar has a first end to which the first pin is coupled and a second end to which the second pin is coupled. The second pivotable bar has a first end to which the second pin is coupled and a second end to which the third pin is coupled. The first coupling has a first end portion arranged to engage the second end of the first bar and a second end portion arranged to engage the first end of the second bar.

The first gas flow unit is arranged when opened to cause the first pin to pivot the first pivotable bar, whereupon the second end of the first pivot bar causes the second pin to prevent the opening of the second gas flow unit and causes the first coupling to pivot to cause the second pivotable bar to pivot, whereupon the second end of the second pivotable bar causes the third pin to prevent the opening of the third gas flow unit.

The second gas flow unit is arranged when opened to cause the second pin to pivot the first and second pivotable bars, whereupon the first end of the first pivot bar causes the first pin to prevent the opening of the first gas flow unit and the second end of the second pivot bar causes the third pin to prevent the opening of the third gas flow unit.

The third gas flow unit is arranged when opened to cause the third pin to pivot the second bar, whereupon the first end of the second pivot bar causes the second pin to prevent the opening of the second gas flow unit and causes the first coupling to pivot to cause the first pivotable bar to pivot, whereupon the first end of the first pivotable bar causes the first pin to prevent the opening of the first gas flow unit.

BRIEF DESCRIPTION OF SEVERAL VIEWS OF THE DRAWINGS

The invention will be described in conjunction with the following drawings in which like reference numerals designate like elements and wherein:

FIG. 1 is a front isometric view of a portion of an anesthesia machine including three removable vaporizer units and an interlock or exclusion system constructed in accordance with one exemplary preferred embodiment of this invention;

FIG. 2 is an enlarged front isometric view of the interlock/exclusion system shown in FIG. 1, with the leftmost vaporizer unit shown being opened to a desired concentration level and the center and rightmost vaporizer units being prevented from being opened by the interlock/exclusion system;

FIG. 3 is a rear isometric view of a portion of the interlock/exclusion system shown in FIG. 2;

FIG. 4 is an isometric view, similar to FIG. 2, but showing the leftmost vaporizer in its closed state;

FIG. 5 is an enlarged vertical sectional view of the relevant portions of the interlock/exclusion system associated with any vaporizer and when that vaporizer is in its closed state, e.g., the vaporizer of FIG. 4; and FIG. 6 is a view similar to FIG. 2, but slightly reduced in size, showing an anesthesia machine having four vaporizers making use of an alternative embodiment of the interlock/exclusion system of this invention.

DETAILED DESCRIPTION OF THE INVENTION

Referring now to the various figures of the drawing wherein like reference characters refer to like parts, there is shown generally at 20 an interlock/exclusion system for use with an a gas administration apparatus, e.g., anaesthesia machine 10. The machine 10 is configured for use with at least three, removable vaporizers 22A, 22B and and 22C. Each vaporizer is identical in construction, except for the particular anesthesia it is arranged to provide to the machine 10 and is arranged to be releasably mounted on the anesthesia machine in a plug-in fashion. In accordance with one preferred exemplary embodiment of this invention each of the vaporizers is a conventional device, such as that sold under the trademark VAPOR 2000 by Draeger Medical, Inc. of Telford, Pa., the assignee of this invention. The anesthesia machine 10 is also a conventional device, such as that sold under the trademark FABIUS GS by the assignee of this invention, except for the interlock/exclusion system 20.

It should also be pointed out at this juncture that while the interlock/exclusion system will be shown and described with reference to anesthesia machines including vaporizer units, the invention is not limited to such uses and can be used in any type of gas administration apparatus making use of three or more removable gas flow units.

Each of the vaporizers 22A–22C is arranged to be removably mounted on the machine to provide its particular anesthesia to the patient when called upon to do so. As is conventional, each vaporizer comprises a canister 24 containing the anesthesia vapor to be dispensed and the means for metering the same into a gas line (not shown) of the anesthesia machine 10. The concentration of the anesthesia vapor provided by each of the vaporizers 22A–22C is determined by the setting of its vapor concentration adjusting dial 26. That dial basically comprises a generally disk-shaped member having a circular, outer surface that is sloped downward and is ribbed to provide a manual gripping. The vaporizer's canister 24 includes an a pointer 28 to indicate the particular vapor concentration setting as established by the vaporizer's dial 26. To that end indicia 30 indicative of the vapor concentration amount are provided along the periphery of the dial 26. In particular, the rotation of the vaporizer dial 26 in the counter-clockwise direction opens the vaporizer to introduce vaporized gas into a patient breathing circuit (not shown) of the machine 10, with the concentration level established by the setting of the dial 26 being displayed or indicated by the particular indicium 30 that is disposed opposite to the pointer 28. Each vaporizer is also arranged to be set to a "transport position" wherein the vaporizer is closed, i.e., no anesthesia will be permitted to exit the vaporizer. When the vaporizer is in this state a transport position mark or indicium 32 on the dial is aligned with the pointer 28. There is also a zero mark indicium 34 on the dial. This indicium is aligned with the pointer when the vaporizer is closed, as best seen in FIG. 4.

As best seen in FIGS. 4 and 5 each vaporizer 22A–22C includes a ring 36 located under its dial 26. The undersurface of each ring 36 includes a recess 38. The recess 38 has a cam surface (ramp) 38A trailing from it to the planar undersurface 40 of the ring 36. The vaporizer's dial 26 engages the ring 36, so that rotation of the dial 26 causes concomitant rotation of the ring 36.

The interlock/exclusion systems of this invention are arranged to enable any vaporizer unit to be opened to a desired concentration level, provided that no other vaporizer unit is already open, and to preclude any vaporizer unit from being opened if one vaporizer unit is already open. Moreover, since the vaporizer units are arranged to be removably mounted on the anesthesia machine, the interlock/exclusion system of this invention is operative to prevent the opening of any vaporizer unit if one is already open, irrespective of whether or not all of the vaporizer units are mounted on the machine. Thus, with the exemplary embodiment of the machine 10, any one of the three vaporizer units 22A–22C can be removed from the machine and the interlock/exclusion system 20 will still be operative to prevent the opening of one of the two remaining vaporizer units in the other of those two vaporizers is open.

It should be pointed out at this juncture that the interlock/exclusion system of this invention can be configured to accommodate any number of removable vaporizer units in excess of two, e.g., the embodiment shown in FIG. 6 accommodates four removable vaporizer units. Moreover, such interlock/exclusion systems are also operative to prevent opening of any vaporizer unit if one vaporizer unit is already open and irrespective of how many vaporizer units are mounted on the machine at the time.

Referring now to FIGS. 2–5, the details of the three vaporizer interlock/exclusion system 20 will now be described. That system basically comprises a vaporizer mount in the form of a bracket 42 (FIG. 5) for mounting the vaporizer units 22A–22C on the machine 10, a pair of elongated pivotable bars 44 and 46, a pivotable coupling 48, and plural pins and associated components (to be described later).

The pivotable bar 44 is an elongated, linear member having a first end 50 and a second end 52 (FIG. 2). The bar is pivotably mounted on the anesthesia machine bracket 42 by a pivot pin 54 extending through the middle of it. Thus, the bar 44 can be pivoted either clockwise or counterclockwise about the pivot axis established by the pivot pin 54. As shown in FIG. 3, the second end 52 of the bar 44 is bifurcated to form a yoke-like structure having a pair of spaced arms 52A and 52B. The space between the arms 52A and 52B is arranged to accommodate a portion of the pivotable coupling 48. The pivotable bar 46 is an elongated member, constructed similar to bar 44 but a mirror image thereof. Thus, the bar 46 has a first end 56 and a second end 58, with the first end 56 of the bar 46 being bifurcated to form a yoke like structure having a pair of spaced arms. The space between those arms is arranged to accommodate another portion of the pivotable coupling 48. The pivotable bar 46 is pivotably mounted on the anesthesia machine bracket 42 by a pivot pin 60 extending through the middle of the bar. Thus, the bar 46 can be pivoted either clockwise or counterclockwise about the pivot axis established by the pivot pin 60.

The pivotable coupling 48 is best seen in FIG. 3 and basically comprises a plate-like, generally T-shaped member having a first end portion in the form of an outwardly extending hook 62 and a second end portion in the form of an outwardly extending hook 64 disposed opposite to and aligned with the first hook 62. The coupling 48 is located between the second end 52 of the first bar 44 and the first end of the second bar 46 to couple those bars together. In particular, the hook 62 of the coupling 48 is disposed in the space between the yoke arms 52A and 52B at the second end 52 of the first pivotable bar 44, while its other hook 64 is disposed in the space between the yoke arms at the first end 56 of the second pivotable bar 46. A pin 66 extends through the arms of the yoke at the second end 52 of the first pivotable bar 44, with the hook 64 of the coupling 48 disposed over and engaging that pin. In a similar manner a pin 68 extends through the arms of the yoke at the first end 56 of the second bar 46, with the hook 64 of the coupling disposed over and engaging that pin.

The coupling 48 is mounted on the anesthesia machine bracket 42 by a pivot pin 70 extending through the middle of the coupling. Thus, the coupling 48 can be pivoted either clockwise or counterclockwise about the pivot axis established by the pivot pin 54.

The interlock/exclusion system 20 includes three follower pins 72, each of which is coupled to a respective one of the vaporizer units 22A–22C. For example, a first of the three follower pins 72 is associated with the first (leftmost) vaporizer unit 22A and is also associated with the first pivotable bar 44. The first follower pin 72 is arranged engage the undersurface of the ring 36 of the vaporizer unit 22A. In particular, the first follower pin 72 is arranged to be disposed within the recess 38 in the ring 36 of the vaporizer unit 22A when that vaporizer unit is closed and to ride down the cam surface 38A onto the underside surface 40 of the ring when that vaporizer unit is opened. The first follower pin 72 is mounted within a first plug-in adaptor 74 associated with the vaporizer 22A. The first adaptor 74 is mounted on the bracket 42. The first follower pin 72 is coupled to the first end 50 of the first pivotable bar 44 by associated pins and components (to be described later).

In a similar manner, a second of the three follower pins 72 is associated with the second vaporizer unit 22B and is also associated with the first pivotable bar 44 and the second pivotable bar 46. The second follower pin 72 is arranged engage the undersurface of the ring 36 of the vaporizer unit 22B. In particular, the second pin 72 is arranged to be disposed within the recess 38 in the ring 36 of the vaporizer unit 22B when that vaporizer unit in closed and to ride down the cam surface 38A onto the underside surface 40 of the ring when that vaporizer unit is opened. The second follower pin 72 is mounted within a second plug-in adaptor 74 that is identical to the first plug-in adaptor. The second plug-in adaptor 74 is associated with the second (middle) vaporizer unit 22B and is also mounted on the anesthesia machine bracket 42. The second follower pin 72 is coupled to the second end 52 of the first pivotable bar 44 and to the first end of the second pivotable bar 46 by associated pins and components (also to be described later).

The third of the three follower pins 72 is associated with the third (rightmost) vaporizer unit 22C and is associated with the second pivotable bar 46. The third follower pin 72 is arranged engage the undersurface of the ring 36 of the vaporizer unit 22C. In particular, the third follower pin 72 is arranged to be disposed within the recess 38 in the ring 36 of the vaporizer unit 22C when that vaporizer unit is closed and to ride down the cam surface 38A onto the underside surface 40 of the ring when that vaporizer unit is opened. The third follower pin 72 is mounted within a third plug-in adaptor 74 that is identical in construction to the first and second plug-in adaptors. The third plug-in adaptor 72 is associated with the third (rightmost) vaporizer unit 22C and is also mounted on the anesthesia machine bracket 42. The third follower pin 72 is coupled to the second end 52 of the second pivotable bar 46 by associated pins and components. Those pins and components, and the pins and components associated with the other vaporizer units will now be described.

The pins and components associated with each of the three vaporizer units are identical. Thus only the group pins and components associated with the first vaporizer unit 22A will be described. Those pins and components are best seen in FIG. 5. Thus, as can be seen in that figure, the each follower pin 72 is a cylindrical member having a domed upper end and a cylindrical lower end. The lower end of the follower pin 72 is fixedly secured within a correspondingly shaped bore (not shown) at the free end of a lever 78. An annular flange extends outward from the follower pin near its lower end. The flange on the lower portion of the pin 72 abuts the top surface of the lever 78, so that the pin projects perpendicularly to the lever. The opposite end of the lever 78 is mounted by a horizontally disposed pivot pin 80 in the plug-in adaptor 74. A slotted set screw 82 is disposed within a threaded bore in the lever 78 adjacent the pin 72 and includes a domed free end extending downward from the undersurface of the lever 78. The domed free end of the set-screw 82 is arranged to abut the top surface of upper intermediate pin 84. The set screw is adjustable to take up any tolerances in the cooperating components. The top surface of the upper intermediate pin 84 is in the form of a flange. The lower end of the upper intermediate pin 84 extends into a central circular bore 86 of a cylindrical sleeve 88. The sleeve 88 is fixedly disposed within a vertically oriented cylindrical bore 90 in the plug-in adaptor 74, and includes an intermediate annular flange 92 for holding it in the desired position. A lower intermediate pin 94 is also located within the circular central bore 90. The lower intermediate pin 94 includes a shoulder 96 at approximately its middle. A helical compression spring 98 is located within the bore 90 extending about the lower intermediate pin 94 and trapped between the shoulder 96 of the pin and an inwardly directed annular flange 100 forming the bottom end of the sleeve 88. The lower end of the lower intermediate pin is press-fit within an a circularly shaped disk or cap 102.

The cap 102 of the assembly of components just described that is associated with the first (leftmost) vaporizer 22A is mounted and located adjacent the first end 50 of the first pivotable bar 44 so that it can engage the top surface thereof (as will be described later). In a similar manner the cap 102 of the assembly of components that is associated with the second (middle) vaporizer 22B is mounted and located so that it is adjacent to the second end 52 of the first pivotable bar 44 and the first end 56 of the second pivotable bar 46. So located the cap is adapted to engage the top surface of the second end 52 of the first pivotable bar 44 and the first end 56 of the second pivotable bar 46 during operation of the interlock/exclusion system (as will also be described later). The cap 102 of the assembly of components that is associated with the third (rightmost) vaporizer 22C is mounted and located so that it is adjacent to the second end 58 of the second pivotable bar 48. So located the cap is adapted to engage the top surface of the second end 58 of the second pivotable bar 46.

Assuming that all of the vaporizer units 22A–22C are closed, the operation of the interlock/exclusion system 20 when the first vaporizer unit 22A is opened will now be discussed. The dial 26 of the vaporizer unit 22A is rotated in a counterclockwise direction from the off position. As the dial begins to rotate, the first follower pin 72 (the pin associated with that vaporizer unit) begins to move out of the recess 38. In particular, the top domed end of that follower pin rides along the upper surface of the recess 38 and then begins riding down the cam surface 38A (see FIG. 4) toward the underside surface 40 of the ring 36. As the follower pin moves (slides) along the cam surface 38A it is pushed downward. Since the follower pin 72 is on the free end of the lever 78, the downward force applied to the follower pin 72 as it rides down the cam surface and onto the undersurface of the ring 36 causes the lever 78 to pivot downward. This downward pivoting of the lever causes the domed end of the set-screw 82 to press downward on the upper intermediate pin 84, whereupon it moves downward vertically, thereby pushing the lower intermediate pin 94 downward against the bias provided by the compression spring 98. The cap 102 on the lower end of the lower intermediate pin engages the top surface of the first end 50 of the first pivotable bar 44, whereupon the first pivotable bar pivots in a counter-clockwise direction.

The pivoting of the first pivot bar 44 in this direction causes its second end 52 to pivot upward, whereupon the top surface of that end engages the cap 102 of the assembly of components associated with the second (middle) vaporizer 22B. This action pushes that cap 102 upward carrying its associated lower intermediate pin 94 upward. The movement of the lower intermediate pin 94 upward pushes the upper intermediate pin 84 upward, thereby pivoting the lever 78 counterclockwise. The counterclockwise pivoting of the lever 78 holds the second follower pin 72 within the recess 38, so that the dial 26 of the second vaporizer unit 22B cannot be opened. Further turning of the dial 26 of the first vaporizer unit 22A establishes the desired rate of flow of anesthesia from it into the patient breathing circuit, while the interlock/exclusion system 20 prevents the other two vaporizer units 22B and 22C from being opened.

The pivoting of the first pivotable bar 44 as described above when the first vaporizer unit 22A is opened also causes the second pivotable bar 46 to be pivoted counter-clockwise with the first pivotable bar. In particular, the upward movement of the second end 52 of the first pivotable bar 44 causes its associated pin 66 to push upward on the hook 62 of the coupling 48, thereby pivoting the coupling in the clockwise direction. This action causes the hook 64 on the opposite side of the coupling to press downward on the pin 68 at the first end 56 of the second pivotable bar 46. Accordingly, the second pivotable bar 46 pivots in the counter-clockwise direction. This action causes the second end 58 of the pivotable bar 46 to engage the cap 102 of the assembly of components associated with the third (rightmost) vaporizer unit 22C, whereupon that assembly of components operates in the same manner as the assembly of components associated with the middle vaporizer unit 22B. Thus, the third follower pin 72 will be held in the recess 38 of the third vaporizer unit 22C to prevent it from being opened.

As will be appreciated by those skilled in the art, the interlock/exclusion system 20 will operate as described to is prevent the opening of the middle vaporizer 22B, even if the rightmost vaporizer 22C has been removed from the anesthesia machine 10. So too, the system 20 will prevent the opening of the rightmost vaporizer unit 22C even if the middle vaporizer 22B has been removed from the anesthesia machine 10.

Assuming that the middle vaporizer unit 22B is the unit desired to be opened, it is necessary to close any vaporizer unit that had previously been opened. Thus, assuming that the leftmost vaporizer unit 22A had been opened (as in the previous example), it will be necessary to close it before opening the middle vaporizer unit 22B. To that end the dial 26 of the leftmost vaporizer unit is rotated in the clock-wise direction whereupon the first follower pin 72 (the pin associated with it) will ride along the undersurface 40 of the ring 36 until it reaches the cam surface 38A. As it begins to ride along the cam surface the bias force provided by the compression spring 98 will drive the upper intermediate pin 84 upward, thereby pivoting the lever 78 in the counter-clockwise direction. This action will push the first pin 72 upward so that it follows the cam surface 38A until it reaches the recess 38, at which time the first vaporizer unit 22A will be closed. At this time all of the vaporizer units will be closed. Thus, one can then rotate the dial 26 of the second (middle) vaporizer unit 22B to open it.

The counter-clockwise rotation of the dial 26 of the middle vaporizer unit 22B, causes the second follower pin (the pin associated with it) to begin to ride on the cam surface 38A of its associated ring 36. As the second follower pin 72 moves along the cam surface 38A it is pushed downward. Since the second follower pin 72 is on the free end of the lever 78, the downward force applied to the second follower pin 72 as it rides down the cam surface 38A and onto the undersurface 40 of the ring 36 causes the lever 78 to pivot downward. This downward pivoting of the lever causes the domed end of the set-screw 82 to press downward on the upper intermediate pin 84, whereupon it moves downward vertically, thereby pushing the lower intermediate pin 94 downward against the bias provided by the compression spring 98. The cap 102 on the lower end of the lower intermediate pin 94 engages the top surface of the second end 52 of the first pivotable bar 44 and the first end 56 of the second pivotable bar 46.

The downward force on the second end of the first pivotable bar 44 pivots it in a clockwise direction. The pivoting of the first pivot bar 44 in this direction causes the top surface of its first end 50 to pivot upward, whereupon it engages the cap 102 of the assembly of components associated with the first vaporizer unit 22A. This action pushes that cap 102 upward carrying its associated lower intermediate pin 94 upward. The movement of the lower intermediate pin upward pushes the upper intermediate pin 84 upward, thereby pivoting the lever 78 counterclockwise. The counterclockwise pivoting of the lever 78 holds the first follower pin 72 within the recess 38, so that the dial 26 of the first vaporizer unit 22A cannot be opened.

The downward force on the first end of the second pivotable bar 46 pivots it in a counter-clockwise direction to cause the top surface of its second end 58 to pivot upward. This action causes that surface to engage the cap 102 of the assembly of components associated with the third vaporizer unit 22C to push that cap 102 upward carrying its associated lower intermediate pin 94 upward. The movement of the lower intermediate pin upward pushes the upper intermediate pin 84 upward, thereby pivoting the lever 78 counter-clockwise. The counterclockwise pivoting of the lever 78 holds the third follower pin 72 within the recess 38, so that the dial 26 of the third vaporizer unit 22C cannot be opened.

Further turning of the dial 26 of the middle vaporizer unit 22B establishes the desired rate of flow of anesthesia therefrom, while the interlock/exclusion system 20 prevents the other two vaporizer units 22A and 22C from being opened.

Operation of the interlock/exclusion system when the third (rightmost) vaporizer unit 22C is similar to the operation of the system when the first (leftmost) vaporizer unit is opened and will not be described in detail in the interest of brevity.

In FIG. 6 there is shown an alternative embodiment of an anesthesia machine making use of four removably mounted vaporizer units 22A–22D and an interlock/exclusion system 20' constructed in accordance with this invention for accommodating those units. The vaporizer units 22A–22D are identical units, and each is constructed in the same manner as described heretofore with reference to the system 20. Moreover, the interlock/exclusion system 20' is identical to the system 20 except that it includes a second pivotable coupling 148, a third pivotable bar 144, a fourth follower pin 172 and an assembly of pins and components associated therewith. In the interests of brevity the common components of the vaporizer units 22A–22D, and the interlock/exclusion systems 20 and 20' will be give n the same reference numbers and a description of their construction, arrangement and operation will not be reiterated.

Turning now to FIG. 6 it can be seen that the second pivotable coupling 148 is located between the second end of the second pivotable bar 46 and the first end of the third pivotable bar 144. The second end of the second pivotable bar is bifurcated to form a yoke like the first end 56 of that bar in order to accommodate the hook 62 of the second pivotable coupling 148 therein. The hook 62 of the second coupling member 148 is disposed over a pin 166 extending through the yoke at the second end 58 of the second pivotable bar 46 to couple that bar to the second coupling 148. The third pivotable bar 144 includes a first end 156 which is bifurcated to form a yoke like the first end of the second pivotable bar in order to accommodate the hook 64 of the second pivotable coupling 148 therein. The hook 64 of the second coupling member 148 is disposed over a pin 168 extending through the yoke at the first end 156 of the third pivotable bar 144 to couple that bar to the second coupling 148. The third pivotable bar 144 is mounted for pivoting about a central pin 160.

The cap 102 of the assembly of components associated with the third vaporizer unit 22C is disposed adjacent the second end 58 of the second pivotable bar 46 and the first end 156 of the third pivotable bar 144 in the same manner as described with reference to the cap 102 of the components associated with the second vaporizer unit 22B. Similarly the cap 102 of the assembly of components associated with the fourth vaporizer unit 22D is disposed adjacent the second end 158 of the third pivotable bar 144 in the same manner as described with reference to the cap 102 of the components associated with the second vaporizer unit 22B of the interlock/exclusion system 20.

With the components of the interlock/exclusion system 20' constructed and arranged as just described the operation of that system will be comparable to the operation of system 20, whereupon the opening of any one vaporizer unit 22A–22D will preclude the opening of any other vaporizer unit until the opened vaporizer is closed and irrespective of whether or not all of the vaporizer units 22A–22D are mounted on the anesthesia machine 10'.

As should be appreciated by those skilled in the art with the anesthesia machine and vaporizer units constructed as just described, wherein the recess and associated cam surface is located in the underside of the vaporizer dial the cannister of the vaporizer would get in the way of components coupling the pivotable bars to the follower pins if those bars were located directly under the follower pins. Thus, as can be seen clearly in FIG. 5, in the embodiments shown herein the vertical plane that pivotable bars 44/46/144 pivot in is laterally offset, e.g., in front of, the plane in which the follower pins 72 associated with the vaporizer units 22A–22D reside. Accordingly, the interlock/exclusion systems of this invention make use of the various pins and components coupling the pivotable bars to the follower pins. For other anesthesia machines and/or other vaporizer units the pivotable bars and the follower pins may be located in a common plane. Thus, it should be apparent that the subject interlock/exclusion system isn't limited to anesthesia machines and/or vaporizer units like those described above. In fact, the interlock/exclusion systems of this invention can make use of follower pins and pivotable bars and pivotable couplings that pivot/reciprocate/move in one or more vertical or horizontal planes.

While the invention has been described in detail and with reference to specific examples thereof, it will be apparent to one skilled in the art that various changes and modifications can be made therein without departing from the spirit and scope thereof.

What is claimed is:

1. An interlock/exclusion system for use with an gas administration apparatus having at least a first, second and third gas flow units removably secured thereto, each of the gas flow units being arranged to be opened to enable the apparatus to provide a gas to a patient, said interlock/exclusion system being arranged when any one of the gas flow units is opened to prevent the opening of the others of the gas flow units, said interlock/exclusion system comprising a first pivotable bar, a second pivotable bar, a first pivotable coupling, a first pin associated with said first bar and with the first gas flow unit, a second pin associated with said first and second bars and said second gas flow unit, a third pin associated with said second bar and said third gas flow unit, said first pivotable bar having a first end to which said first pin is coupled and a second end to which said second pin is coupled, said second pivotable bar having a first end to which said second pin is coupled and a second end to which said third pin is coupled, said first coupling having a first portion arranged to engage said second end of said first pivotable bar and a second portion arranged to engage said first end of said second pivotable bar, said first gas flow unit being arranged when opened to cause said first pin to pivot said first pivotable bar, whereupon said second end of said first pivotable bar causes said second pin to prevent the opening of said second gas flow unit and causes said first coupling to pivot to cause said second pivotable bar to pivot, whereupon said second end of said second pivotable bar causes said third pin to prevent the opening of said third gas flow unit, said second gas flow unit being arranged when opened to cause said second pin to pivot said first and second pivotable bars, whereupon said first end of said first pivotable bar causes said first pin to prevent the opening of said first gas flow unit and said second end of said second pivotable bar causes said third pin to prevent the opening of said third gas flow unit, said third gas flow unit being arranged when opened to cause said third pin to pivot said second pivotable bar, whereupon said first end of said second pivotable bar causes said second pin to prevent the opening of said second gas flow unit and causes said first coupling to pivot to cause said first pivotable bar to pivot, whereupon said first end of said first pivotable bar causes said first pin to prevent the opening of said first gas flow unit.

2. The interlock/exclusion system of claim 1 wherein each of said pivotable bars is an elongated member having an intermediate pivot point located between its first end and its second end.

3. The interlock/exclusion system of claim 2 wherein said first coupling comprises a pivotable member having an opposed pair of hooks projecting from opposite sides of a pivot point, one of said hooks being arranged to releasably engage said second end of said first pivotable bar, the other of said hooks being arranged to releasably engage said first end of said second pivotable bar.

4. The interlock/exclusion system of claim 3 where said first coupling is a generally T-shaped member, whose pivot point is located between and below said second end of said first pivotable bar and said first end of said second pivotable bar.

5. The interlock/exclusion system of claim 1 wherein the gas administration apparatus includes a fourth gas flow unit and wherein said interlock/exclusion system additionally comprises a third pivotable bar, a second pivotable coupling, and a fourth pin, said fourth pin being associated with said third pivotable bar and with said fourth gas flow unit, said third pivotable bar having a first end to which said third pin is coupled and a second end to which said fourth pin is coupled, said second coupling having a first portion arranged to engage said second end of said second pivotable bar and a second portion arranged to engage said first end of said third pivotable bar, said fourth gas flow unit being arranged when opened to cause said fourth pin to pivot said third pivotable bar, whereupon said first end of said third pivotable bar causes said third pin to prevent the opening of said third gas flow unit and causes said second coupling to pivot to cause said second pivotable bar to pivot, whereupon said first end of said second pivotable bar causes said second pin to prevent the opening of said second gas flow unit, and causes said first coupling to pivot to cause said first pivotable bar to pivot, whereupon said first end of said first pivotable bar causes said first pin to prevent the opening of said first gas flow unit.

6. The interlock/exclusion system of claim 5 wherein each of said pivotable bars is an elongated member having an intermediate pivot point located between its first end and its second end.

7. The interlock/exclusion system of claim 6 wherein said first coupling comprises a pivotable member having an opposed pair of hooks projecting from opposite sides of a pivot point, one of said hooks of said first coupling being arranged to releasably engage said second end of said first pivotable bar, the other of said hooks of said first coupling being arranged to releasably engage said first end of said second pivotable bar and wherein said second coupling comprises a pivotable member having an opposed pair of hooks projecting from opposite sides of a pivot point, one of said hooks of said second coupling being arranged to releasably engage said second end of said second pivotable bar, the other of said hooks of said second coupling being arranged to releasably engage said first end of said third pivotable bar.

8. The interlock/exclusion system of claim 7 wherein said first coupling is a generally T-shaped member, whose pivot point is located between and below said second end of said first bar and said first end of said second bar, and wherein said second coupling is a generally T-shaped member, whose pivot point is located between and below said second end of said second bar and said first end of said third bar.

9. The interlock/exclusion system of claim 1 wherein each of the gas flow units includes a rotatable cap having a recess in its periphery, each of the recesses including a cam surface, and wherein said first, second and third pins are adapted to enter into an associated one of said recesses.

10. The interlock/exclusion system of claim 9 additionally comprising first, second and third intermediate members, said first intermediate member being arranged to be engaged by said first end of said first pivotable bar and being coupled to said first pin, said second intermediate member being arranged to be engaged by said first end of said second pivotable bar and said second end of said first pivotable bar, said second intermediate member being coupled to said second pin, said third intermediate member being arranged to be engaged by said second end of said second pivotable bar and being coupled to said third pin.

11. The interlock/exclusion system of claim 10 wherein each of said first, second and third intermediate members is oriented vertically, wherein each of said first second and third pins is oriented for generally vertical reciprocation, and wherein each of said recesses is located on an undersurface of the cap of the associated gas flow unit for receipt of a respective one of said first, second and third pins therein.

12. The interlock/exclusion system of claim 11 wherein each of said pivotable bars is an elongated member having an intermediate pivot point located between its first end and its second end.

13. The interlock/exclusion system of claim 12 wherein said first coupling comprises a pivotable member having an opposed pair of hooks projecting from opposite sides of a pivot point, one of said hooks being arranged to releasably engage said second end of said first pivotable bar, the other of said hooks being arranged to releasably engage said first end of said second pivotable bar.

14. The interlock/exclusion system of claim 13 where said first coupling is a generally T-shaped member, whose pivot point is located between and below said second end of said first pivotable bar and said first end of said second pivotable bar.

15. The interlock/exclusion system of claim 11 wherein said first, second and third pins are laterally offset from said first, second, and third intermediate members, respectively, and wherein said interlock/exclusion system additionally comprises a first lever coupled between said first pin and said first intermediate member, a second lever coupled between said second pin and said second intermediate member, and a third lever coupled between said third pin and said third intermediate member.

16. The interlock/exclusion system of claim 15 wherein each of said pivotable bars is an elongated member having an intermediate pivot point located between its first end and its second end.

17. The interlock/exclusion system of claim 16 wherein said first coupling comprises a pivotable member having an opposed pair of hooks projecting from opposite sides of a pivot point, one of said hooks being arranged to releasably engage said second end of said first pivotable bar, the other of said hooks being arranged to releasably engage said first end of said second pivotable bar.

18. The interlock/exclusion system of claim 17 where said first coupling is a generally T-shaped member, whose pivot point is located between and below said second end of said first pivotable bar and said first end of said second pivotable bar.

19. An gas administration apparatus having at least a first, second and third gas flow units removably secured thereto and an interlock/exclusion system, each of said gas flow units being arranged to be opened to enable the apparatus to provide a gas to a patient, said interlock/exclusion system being arranged when any one of said gas flow units is opened to prevent the opening of the others of said gas flow units, said interlock/exclusion system comprising a first pivotable bar, a second pivotable bar, a first pivotable coupling, a first pin associated with said first pivotable bar and with said first gas flow unit, a second pin associated with said first and second pivotable bars and said second gas flow unit, a third pin associated with said second pivotable bar and said third gas flow unit, said first pivotable bar having a first end to which said first pin is coupled and a second end to which said second pin is coupled, said second pivotable bar having a first end to which said second pin is coupled and a second end to which said third pin is coupled, said first coupling having a first portion arranged to engage said second end of said first pivotable bar and a second portion arranged to engage said first end of said second pivotable bar, said first gas flow unit being arranged when opened to cause said first pin to pivot said first pivotable bar, whereupon said second end of said first pivotable bar causes said second pin to prevent the opening of said second gas flow unit and causes said first coupling to pivot to cause said second pivotable bar to pivot, whereupon said second end of said second pivotable bar causes said third pin to prevent the opening of said third gas flow unit, said second gas flow being arranged when opened to cause said second pin to pivot said first and second pivotable bars, whereupon said first end of said first pivotable bar causes said first pin to prevent the opening of said second gas flow unit and said second end of said second pivotable bar causes said third pin to prevent the opening of said third gas flow unit, said third gas flow unit being arranged when opened to cause said third pin to pivot said second pivotable bar, whereupon said first end of said second pivotable bar causes said second pin to prevent the opening of said second gas flow unit and causes said first coupling to pivot to cause said first pivotable bar to pivot, whereupon said first end of said first pivotable bar causes said first pin to prevent the opening of said first gas flow unit.

20. The gas administration apparatus of claim 19 wherein each of said pivotable bars is an elongated member having an intermediate pivot point located between its first end and its second end.

21. The gas administration apparatus of claim 20 wherein said first coupling comprises a pivotable member having an opposed pair of hooks projecting from opposite sides of a pivot point, one of said hooks being arranged to releasably engage said second end of said first pivotable bar, the other of said hooks being arranged to releasably engage said first end of said second pivotable bar.

22. The gas administration apparatus of claim 21 where said first coupling is a generally T-shaped member, whose pivot point is located between and below said second end of said first pivotable bar and said first end of said second pivotable bar.

23. The gas administration apparatus of claim 19 wherein the gas administration apparatus includes a fourth gas flow unit and wherein said interlock/exclusion system additionally comprises a third pivotable bar, a second pivotable coupling, and a fourth pin, said fourth pin being associated with said third pivotable bar and with said fourth gas flow unit, said third pivotable bar having a first end to which said third pin is coupled and a second end to which said fourth pin is coupled, said second coupling having a first portion arranged to engage said second end of said second pivotable bar and a second portion arranged to engage said first end of said third pivotable bar, said fourth gas flow unit being arranged when opened to cause said fourth pin to pivot said third pivotable bar, whereupon said first end of said third pivotable bar causes said third pin to prevent the opening of said third gas flow unit and causes said second coupling to pivot to cause said second pivotable bar to pivot, whereupon said first end of said second pivotable bar causes said second pin to prevent the opening of said second gas flow unit, and causes said first coupling to pivot to cause said first pivotable bar to pivot, whereupon said first end of said first pivotable bar causes said first pin to prevent the opening of said first gas flow unit.

24. The anesthesia of claim 19 wherein each of the gas flow units includes a rotatable cap having a recess in its periphery, each of the recesses including a cam surface, and wherein said first, second and third pins are adapted to enter into an associated one of said recesses.

25. The gas administration apparatus of claim 24 additionally comprising first, second and third intermediate members, said first intermediate member arranged to be engaged by said first end of said first pivotable bar and being coupled to said first pin, said second intermediate member arranged to be engaged by said first end of said second pivotable bar and said second end of said first pivotable bar, said second intermediate member being coupled to said second pin, said third intermediate member arranged to be engaged by said second end of said second pivotable bar and being coupled to said third pin.

26. The gas administration apparatus of claim 25 wherein each of said first, second and third intermediate members is oriented vertically, wherein each of said first second and third pins is oriented for generally vertical reciprocation, and wherein each of said recesses is located on an undersurface of the cap of the associated gas flow unit for receipt of a respective one of said first, second and third pins therein.

27. The gas administration apparatus of claim 26 wherein said first, second and third pins are laterally offset from said first, second, and third intermediate members, respectively, and wherein said interlock/exclusion system additionally comprises a first lever coupled between said first pin and said first intermediate member, a second lever coupled between said second pin and said second intermediate member, and a third lever coupled between said third pin and said third intermediate member.

* * * * *